(12) United States Patent
Reydel (10) Patent No.: US 8,366,673 B2
(45) Date of Patent: Feb. 5, 2013

(54) METHOD AND DEVICES FOR SELECTIVE ENDOSCOPIC RETROGRADE CHOLANGIOPANCREATOGRAPHY

(75) Inventor: Boris Reydel, West Caldwell, NJ (US)

(73) Assignee: Cook Medical Technologies LLC, Bloomington, IN (US)

( * ) Notice: Subject to any disclaimer, the term of this patent is extended or adjusted under 35 U.S.C. 154(b) by 595 days.

(21) Appl. No.: 11/883,300

(22) PCT Filed: Jan. 13, 2006

(86) PCT No.: PCT/US2006/001136
§ 371 (c)(1),
(2), (4) Date: Feb. 1, 2008

(87) PCT Pub. No.: WO2006/088578
PCT Pub. Date: Aug. 24, 2006

(65) Prior Publication Data
US 2008/0306467 A1 Dec. 11, 2008

Related U.S. Application Data

(60) Provisional application No. 60/649,101, filed on Feb. 3, 2005.

(51) Int. Cl.
*A61M 5/178* (2006.01)
(52) U.S. Cl. .................. 604/164.04; 604/93.01
(58) Field of Classification Search .......... 604/105–109, 604/115, 164.04, 176, 93.01
See application file for complete search history.

(56) References Cited

U.S. PATENT DOCUMENTS

| | | | | |
|---|---|---|---|---|
| 3,548,830 A | * | 12/1970 | Brinckmann et al. | 606/125 |
| 3,626,950 A | * | 12/1971 | Schulte | 604/268 |
| 5,071,412 A | * | 12/1991 | Noda | 604/268 |
| 5,188,595 A | * | 2/1993 | Jacobi | 604/509 |
| 5,769,821 A | | 6/1998 | Abrahamson et al. | |
| 5,972,013 A | * | 10/1999 | Schmidt | 606/185 |
| 6,071,295 A | * | 6/2000 | Takahashi | 606/191 |
| 6,139,522 A | * | 10/2000 | Weldon et al. | 604/93.01 |
| 6,355,031 B1 | * | 3/2002 | Edwards et al. | 606/31 |
| 2001/0025161 A1 | * | 9/2001 | Martinez | 604/284 |
| 2003/0073955 A1 | * | 4/2003 | Otawara | 604/164.01 |
| 2004/0122421 A1 | * | 6/2004 | Wood | 606/41 |
| 2004/0133198 A1 | * | 7/2004 | Deal et al. | 606/47 |
| 2004/0249362 A1 | * | 12/2004 | Levine et al. | 604/523 |

OTHER PUBLICATIONS

"Ampulla". American Heritage Dictionary of the English Language. <http://education.yahoo.com/reference/dictionary/entry/ampulla>.*
May 25, 2006 PCT International Search Report in PCT International Application No. PCT/US2006/001136.

* cited by examiner

*Primary Examiner* — Kevin C Sirmons
*Assistant Examiner* — Kami A Bosworth
(74) *Attorney, Agent, or Firm* — Brinks Hofer Gilson & Lione (57) ABSTRACT

A catheter for inserting into a bodily structure. The catheter includes a primary lumen and a secondary lumen having a side hole for engaging under negative pressure with an inter-mural mucosa of the bodily structure. Methods of use of a catheter involving insertion of the catheter into a bodily structure and engaging the catheter under negative pressure with an inter-mural mucosa of the bodily structure.

6 Claims, 12 Drawing Sheets

METHOD AND DEVICES FOR SELECTIVE ENDOSCOPIC RETROGRADE CHOLANGIOPANCREATOGRAPHY

REFERENCE TO RELATED APPLICATION

This application is a §371 National Stage of PCT International Application No. PCT/US2006/001136, filed Jan. 13, 2006, which claims benefit of U.S. Provisional Application No. 60/649,101, filed Feb. 3, 2005 the contents of all of which are hereby incorporated by reference into this application.

BACKGROUND

1. Technical Field

The present disclosure relates to endoscopic retrograde cholangiopancreatography and, more specifically, to methods and devices for selective endoscopic retrograde cholangiopancreatography.

2. Description of the Related Art

Endoscopic retrograde cholangiopancreatography (ERCP) is the visualization of the pancreatic and biliary ducts by means of endoscopic injection of a contrast medium through the hepatopancreatic ampulla (the ampulla of Vater). A retrograde image of both structures can be formed on an X-ray. ERCP may be used to facilitate the diagnosis of obstructions, for example, gallstones or cholangiocarcinoma.

In performing ERCP, an endoscope or catheter may be inserted through the mouth of the patient, down the esophagus, through the stomach, through the pylorus into the duodenum to the ampulla. A catheter or cannulatome may be inserted through the lumen of the endoscope or catheter to the ampulla to deliver radiocontrast into the bile ducts and/or pancreatic duct. The structures receiving radiocontrast may then be visualized by X-ray imaging techniques such as fluoroscopy.

Devices such as a catheter, guidewire, papillotome, etc. may be sent through the lumen of the endoscope or catheter for purposes such as radiocontrast delivery, specimen biopsy, etc. These devices may become obstructed by folds of the mucosa inside the ampullae that are either natural or an effect of the endoscope and/or its device's wrinkling of the mucosa as it is inserted into the ampullae. Similar folding may occur in the intra-mural portion of the CBD and/or pancreatic duct.

Figure 1:
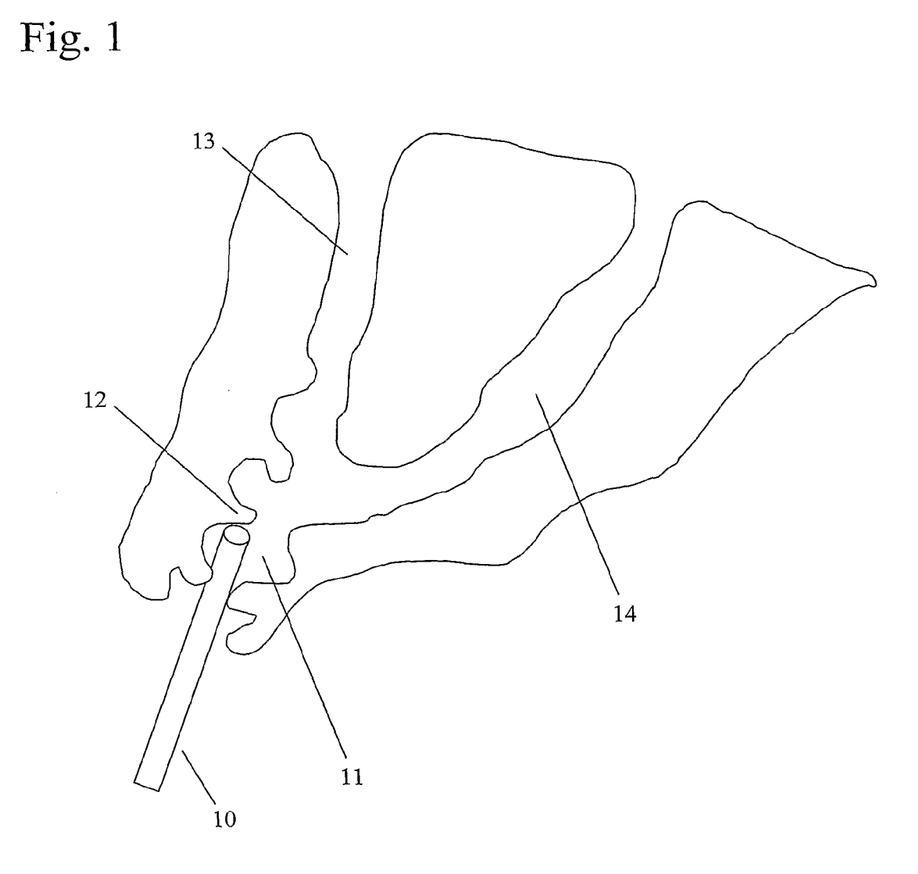
FIG. 1 is a diagram illustrating endoscope/catheter redundant mucosa fold obstruction.

FIG. 1 is a diagram illustrating endoscopelcatheter redundant mucosa fold obstruction. As an endoscope or catheter 10 is inserted into the ampullae 11, the CBD 13 and/or the pancreatic duct 14, folds 12 within the inner-lining of the structures may form. These folds 12 may obstruct the endoscope or catheter 10 and/or a device such as a catheter, guidewire, papillotome, etc. that may be inserted through the endoscope or catheter 10.

As these folds may complicate ERCP, it is desirable to use a method and device for straightening out folds within the ampullae, bile ducts and/or pancreatic duct when performing ERCP.

SUMMARY

A catheter for inserting into a bodily structure. The catheter includes a primary lumen for passing a device. One or more flaps or circumferential anchors protrude from a front tip of the catheter. The flaps or circumferential anchors engage with an inter-mural mucosa of the bodily structure.

A catheter for inserting into a bodily structure includes a primary lumen for passing a device and one or more secondary lumens with negative pressure for engaging with an inter-mural mucosa of the bodily structure.

A method for inserting a catheter into a bodily structure includes inserting a catheter with one or more flaps or circumferential anchors protruding from a front tip of the catheter into the bodily structure. The catheter is pulled back to engage the one or more flaps or circumferential anchors with an inter-mural mucosa of the bodily structure. The inter-mural mucosa is thereby pulled taut. A device is inserted through a primary lumen of the catheter into the bodily structure.

A method for inserting a catheter into a bodily structure includes inserting a catheter into the bodily structure. One or more points of negative pressure on the catheter are activated to engage an inter-mural mucosa of the bodily structure. The catheter is pulled back to pull the inter-mural mucosa taut. A device is inserted through a primary lumen of the catheter into the bodily structure.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DETAILED DESCRIPTION

In describing the preferred embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Embodiments of the present invention seek to straighten out folds within the inner walls of bodily structures, for example, the ampullae, bile ducts and/or pancreatic duct, for example, when performing ERCP. As mentioned above, the folds may be preexisting or may be caused by the insertion of a catheter into the structure. For example, as the catheter is inserted into the structure, the inner walls of the structure may be pushed upwards causing a buckling resulting in the folding of the inner walls of the structure.

Embodiments of the present invention may straighten the folds by pulling the inner surface of the structure, for example, the inter-mural mucosa of the ampullae, bile ducts and/or pancreatic duct, tout and smooth. Insertion if a device such as a catheter, guidewire, papillotome may then be facilitated by the removal of potentially obstructive wrinkles. For example, ERCP may be performed.

Figure 2:
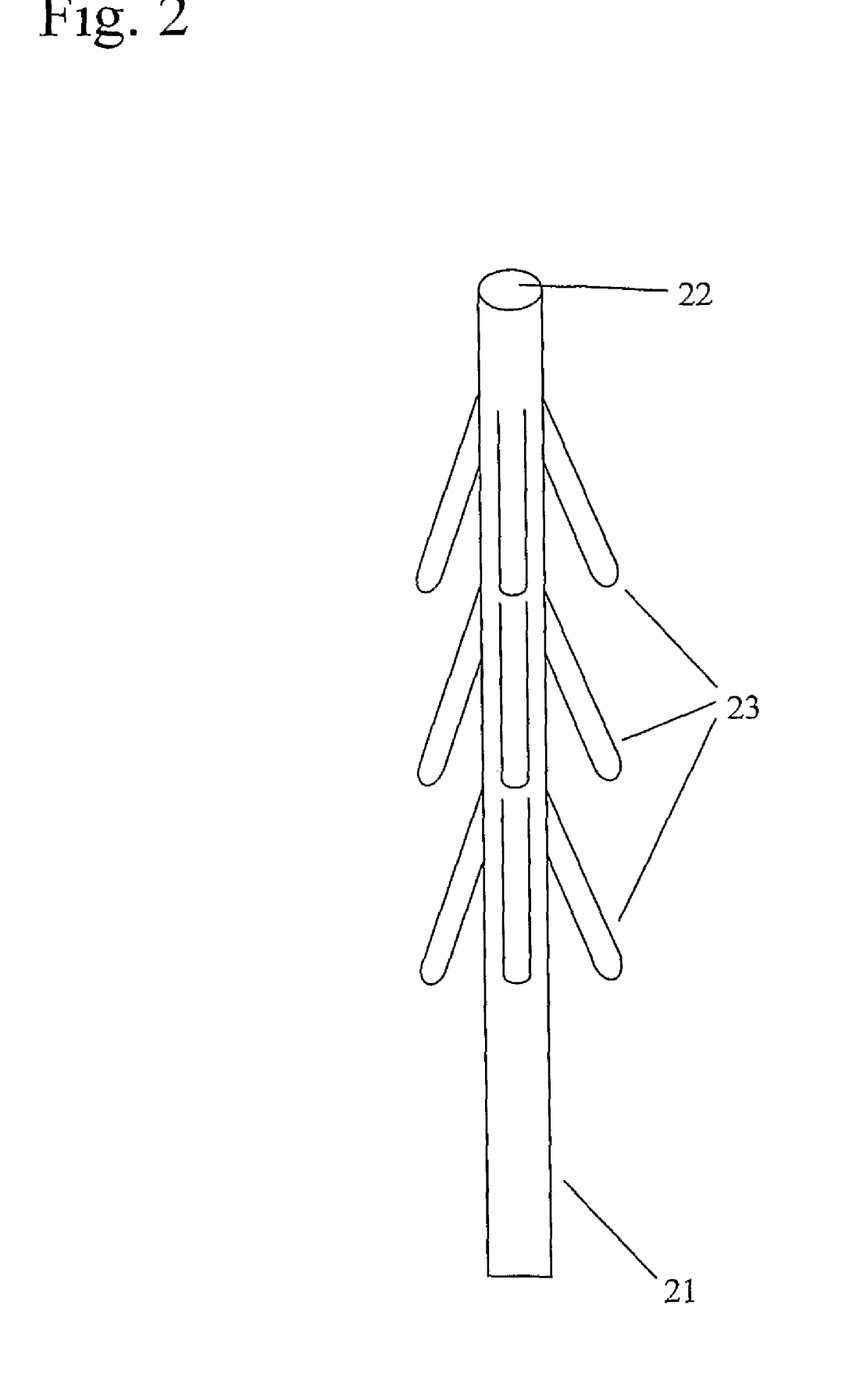
FIG. 2 is a diagram showing a specialized ERCP catheter according to an embodiment of the present invention.

A specialized ERCP catheter may be used to straighten out wrinkles within the inter-mural mucosa of the ampullae, bile ducts and/or pancreatic duct. FIG. 2 is a diagram showing a specialized ERCP catheter according to an embodiment of the present invention. The specialized ERCP catheter 21 may have a tip opening 22 for protrusion of a device such as a catheter, guidewire, papillotome, or contrast injection. The front tip of the catheter 21 may have one or more rows of flaps or petals 23 (referred to herein as flaps) around the perimeter of the catheter. There may be a number of rows of flaps 23. For example, there may be 1, 2, or three rows of flaps 23. Each row of flaps 23 may have a number of flaps 23, for example, each row may have 1, 2, 3 or 4 flaps 23. The flaps 23 may have a flat and/or blunt ends for engaging the redundant mucosa, for example, within the ampullae. The catheter 21 may then be gently pulled back. As the catheter 21 is pulled back, the flaps 23 engage with the redundant mucosa and may pull the inner surface of the ampullae tout and smooth thereby minimizing the number and size of wrinkles within the intramural mucosa that may potentially obstruct the catheter and/or the protruding device.

According to one embodiment of the present invention, the flaps may be incomplete, meaning that the flaps are shaped to push into the thickness of the inter-mural mucosa without cutting into the internal lumen of the bodily structure, for example, the ampullae. According to another embodiment of the present invention, the flaps may be complete, meaning that the flaps are shaped to cut into the internal lumen of the bodily structure.

Figure 3:
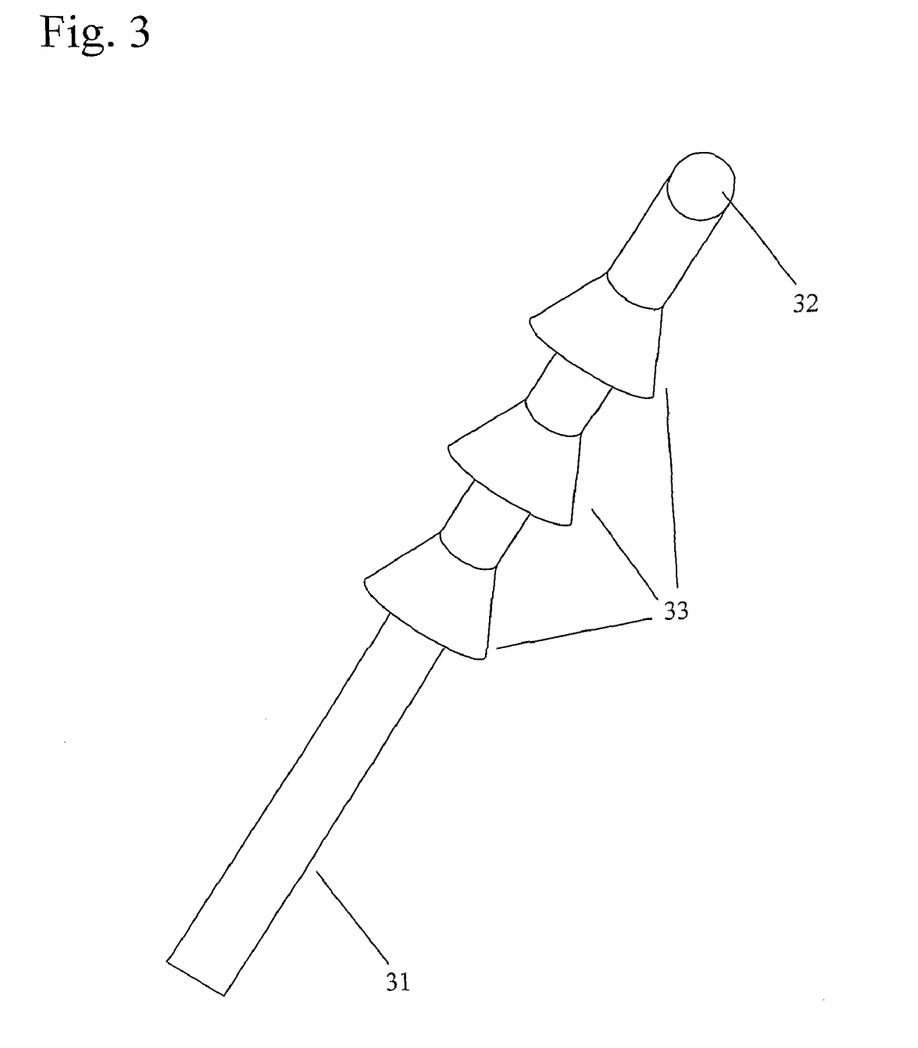
FIG. 3 is a diagram showing a specialized ERCP catheter with complete flaps according to an embodiment of the present invention.

Embodiments of the present invention may use circumferential anchors rather than or in addition to flaps. FIG. 3 is a diagram showing a specialized ERCP catheter with circumferential anchors according to an embodiment of the present invention. The catheter 31 may have a top opening 32 for protrusion of a device such as a catheter, guidewire, papillotome, or contrast injection. The front tip of the catheter 31 may have one or more circumferential anchors 33 around the perimeter of the catheter 31. The circumferential anchors 33 may extend 360 degrees around the entire circumpherence of the catheter 31. For example, there may be 1, 2 or 3 circumferential anchors 33. The circumferential anchors 33 may either be fully enclosed raised cone or may be thin and without volume. The circumferential anchors 33 may have a flat and/or blunt ends for engaging the redundant mucosa, for example, within the ampullae. The catheter 31 may then be gently pulled back. As the catheter 31 is pulled back, the circumferential anchors 33 engage with the redundant mucosa and may pull the inner surface of the ampullae tout and smooth thereby minimizing the number and size of the wrinkles.

Figure 4A:
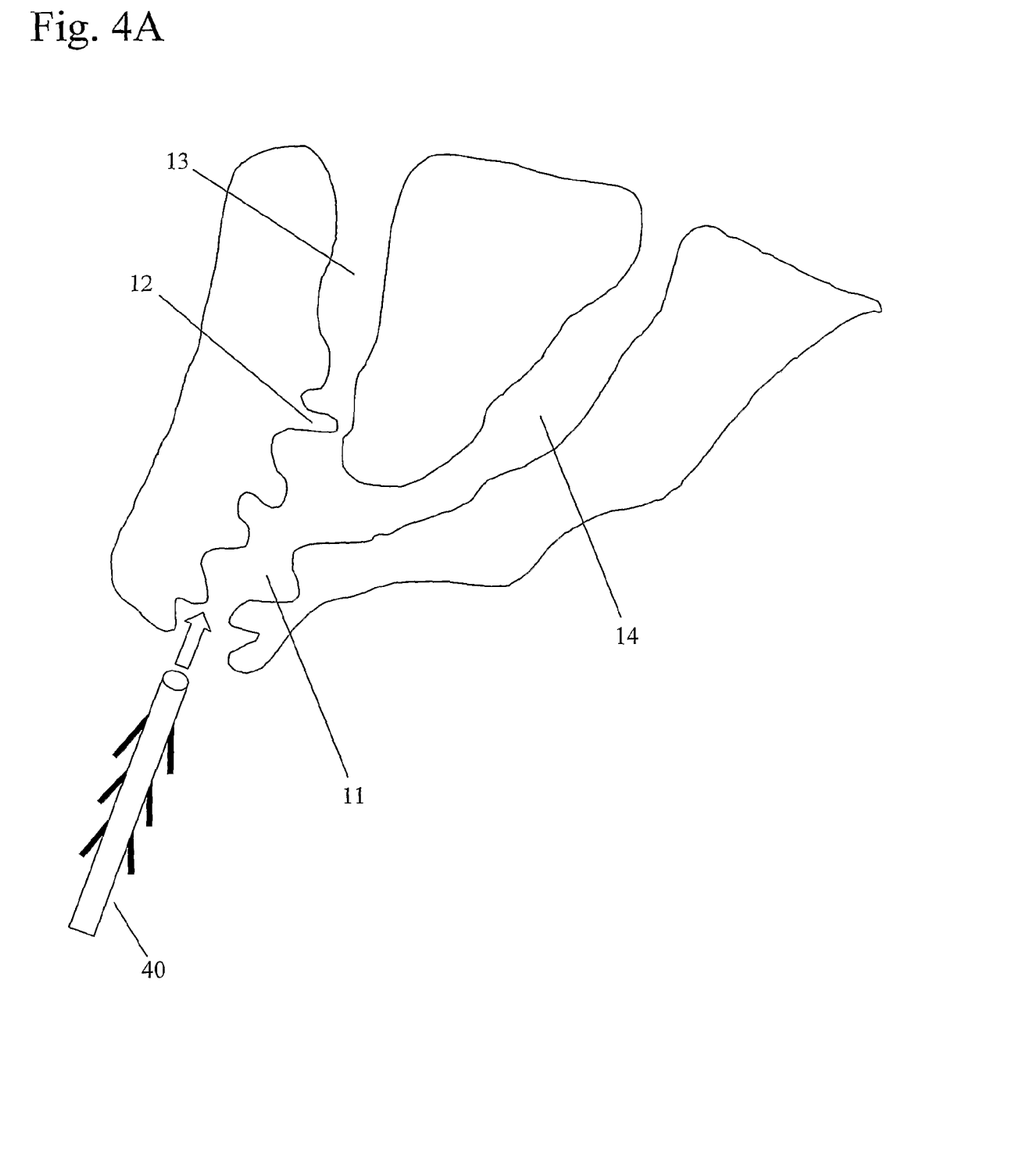
FIGS. 4A, 4B, and 4C show a method for using a specialized catheter to straighten out wrinkles within the inter-mural mucosa of the ampullae, bile ducts and/or pancreatic duct according to an embodiment of the present invention.
Figure 4B:
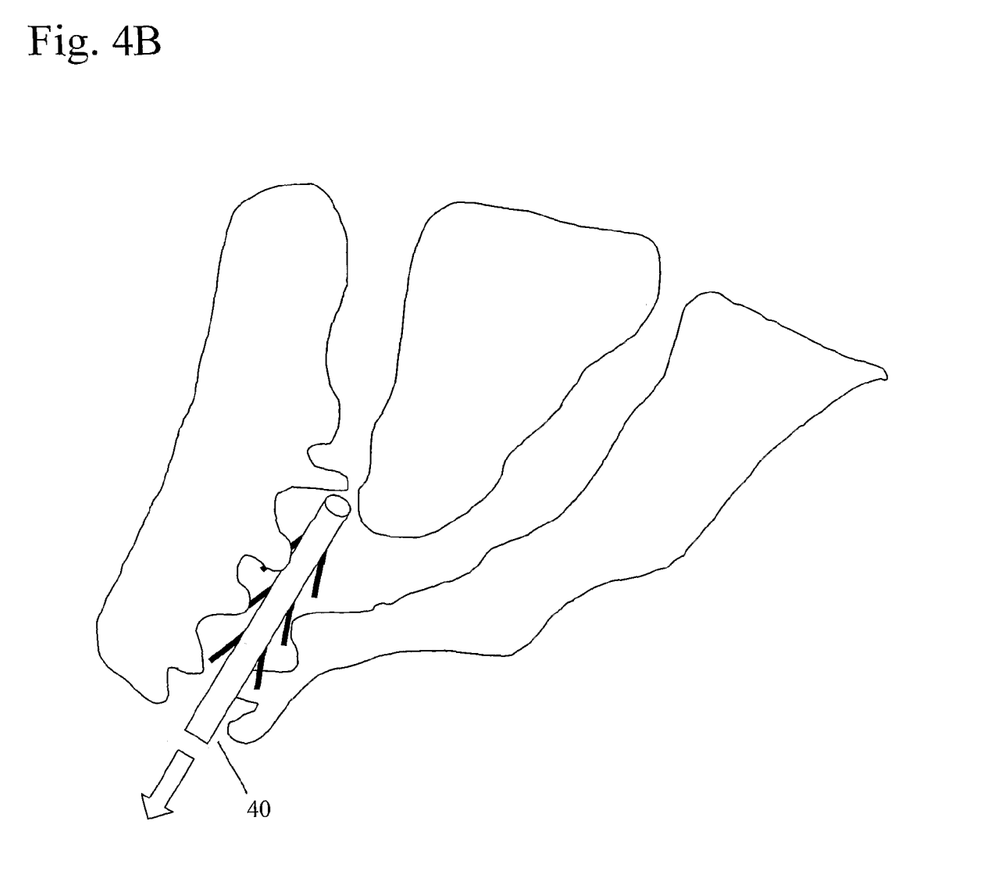
Figure 4C:
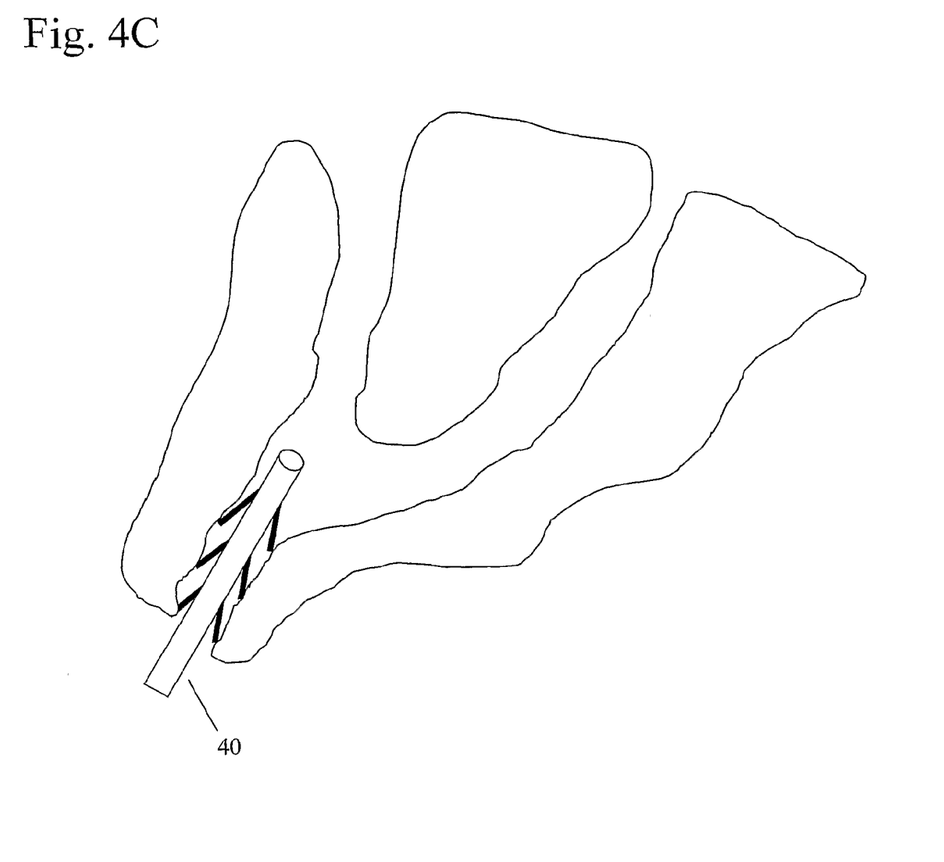

FIGS. 4A, 4B, and 4C show a method for using a specialized catheter to straighten out wrinkles within the inter-mural mucosa of the ampullae, bile ducts and/or pancreatic duct according to an embodiment of the present invention. Referring to FIG. 4A, the specialized catheter 40 may be inserted into, for example, the ampullae 11, the CBD 13 and/or the pancreatic duct 14. As the catheter 40 is inserted, folds 12 may appear in the inter-mural surface of the structure.

FIG. 4B shows the catheter 40 inserted into the ampullae 11. For example, the tip of the catheter 40 may be inserted 2-5 mm into the ampullary orifice. Once the catheter 40 has been inserted, the catheter may be gently pulled back. The blunt ends of the catheter's flaps and/or circumferential anchors may engage the redundant mucosa inside the ampullae. The flaps and/or circumferential anchors may then function as gentle hooks or anchors around the perimeter of the tip of the catheter to taut and straighten the redundant mucosa more distal to the flaps and/or circumferential anchors.

The pulling motion may minimize the number and size of the folds and may thereby minimize obstruction as seen in FIG. 4C. By straightening the ampullae, folding may also be reduced in the CBD and/or the pancreatic duct. After the structures have been straightened, a guidewire may be advanced through the catheter and/or a contrast may be injected. Thus, the wire's tip could straighten the lumen of the structure and more easily travel through the structure without getting stuck on a wrinkle.

The number and position of the flaps and/or circumferential anchors around the catheter's tip's perimeter may be varied to achieve the desired degree to which the lumen of the structure is opened. For example, a flap placed at the 11 o'clock orientation may make a biliary cannulation more plausible while a flap placed at the 3 o'clock orientation make a pancreatic cannulation more plausible.

The catheter its self may be single-, two-, or three-channeled for simultaneous use with wires and contrast. The flaps and/or circumferential anchors of the present invention may also be applied in the papillotomes.

Figure 5A:
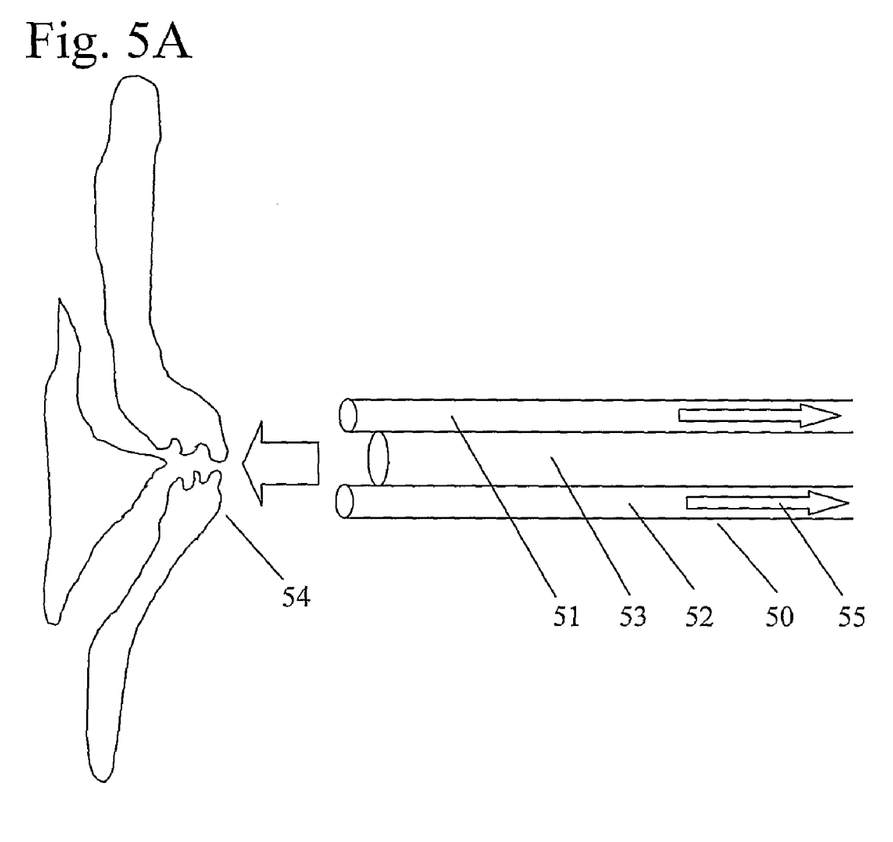
FIGS. 5A and 5B show a specialized catheter according to such an embodiment of the present invention.
Figure 5B:
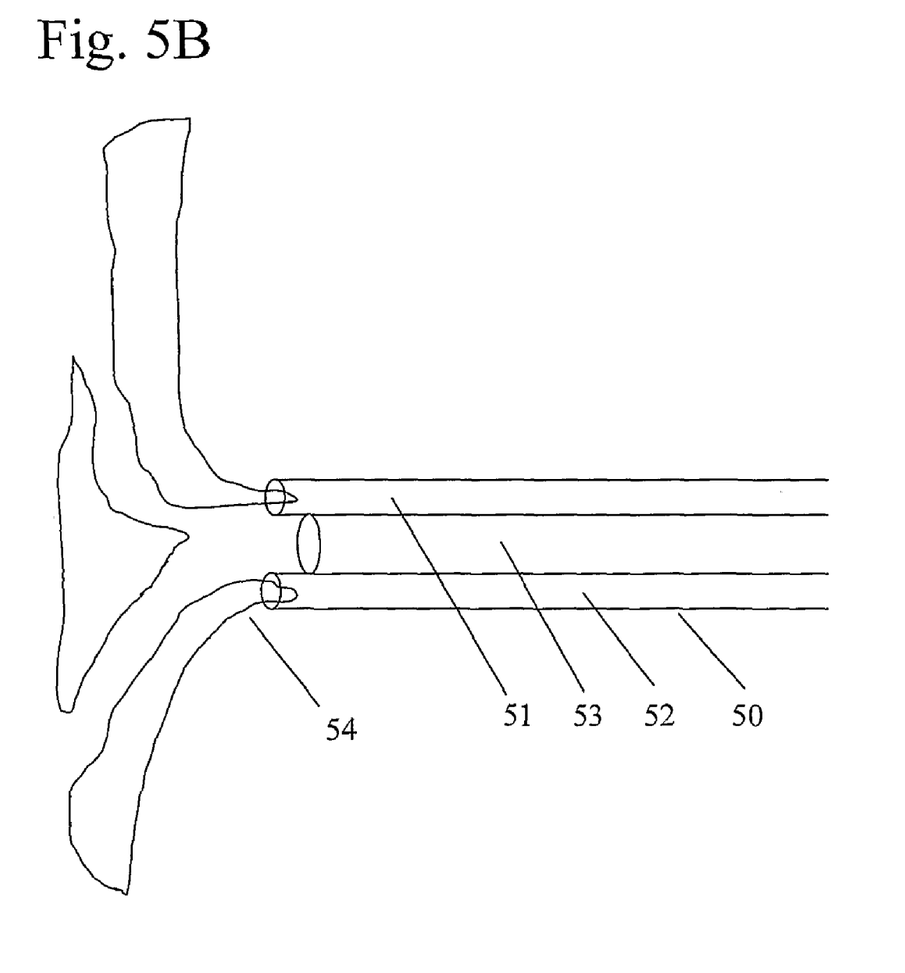

Other embodiments of the present invention may minimize mucosal folds by engaging the rim of the ampullae and pulling it out and open while a thinner catheter and/or guidewire is passed through the taut internal canal. FIGS. 5A and 5B show a specialized catheter according to such an embodiment of the present invention. FIG. 5A shows the specialized catheter 50 approaching the ampullae 54. The catheter 50 may contain one or more suction channels 51 and 52. For example, there may be two suction channels 51 and 52 positioned at 9 and 3 o'clock, or at 11 o'clock for selective bile duct cannulation. The suction channels 51 and 52 may deliver negative pressure suction 55 to create points of negative pressure at the tips of the suction channels 51 and 52. As the catheter 50 approaches the ampullae 54, the rim of the ampullae 54 may be pulled into the suction channels 51 and 52 by the negative pressure suction 55, as seen in FIG. 5B. This pulling of the rim of the ampullae 54 may pull the redundant mucosa tout thereby minimizing wrinkles. A device, for example a catheter, guidewire, papillotome, or contrast injection may then be sent through the inner lumen 53 of the catheter 50, for example, to perform ERCP. Afterwards, the suction 55 may be discontinues to release the ampullae 54 to facilitate removal of the catheter 50. To minimize the risk of undesired engagement of the mucosa, the suction may be inactive during caterer 50 insertion.

Figure 6:
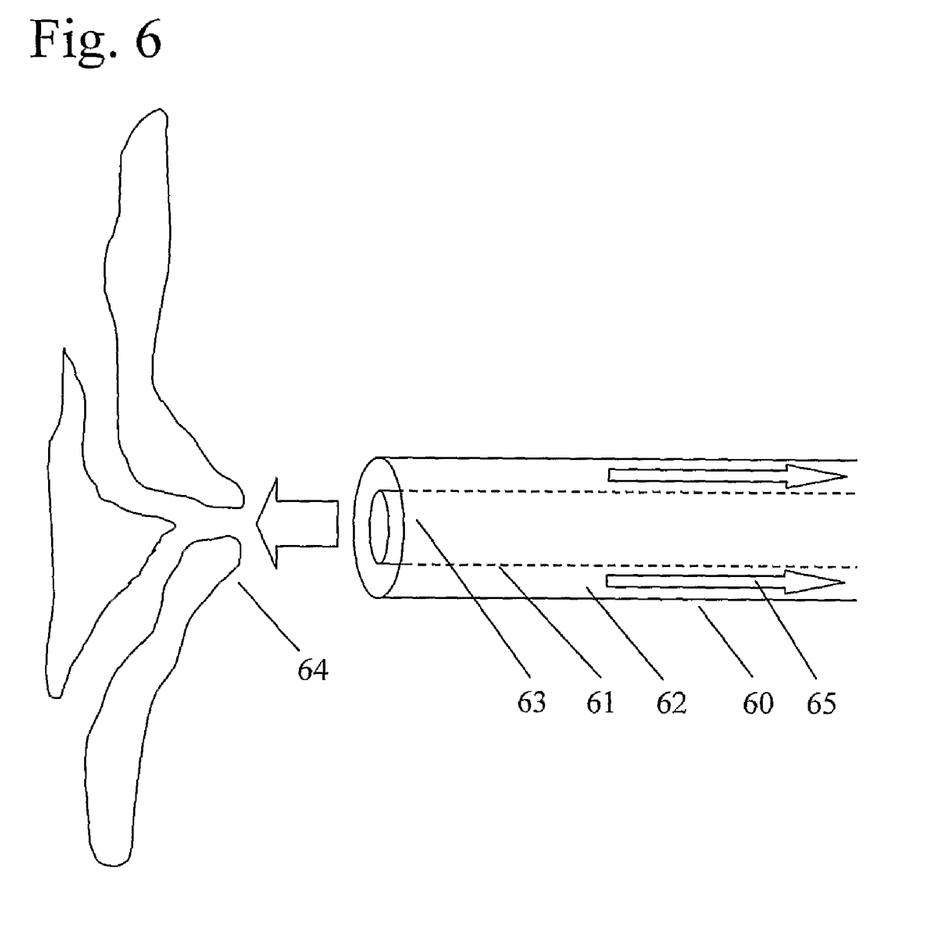
FIG. 6 shows a double-walled catheter that may be used according to an embodiment of the present invention.

According to another embodiment of the present invention, a double-walled catheter may be used. An example of such an embodiment is shown in FIG. 6. Here, a double-walled catheter 60 includes an outer passageway 62 and an inner passageway 63 separated by an inner catheter 61. Negative pressure suction 65 may be applied to the outer passageway 62 to create a point of negative pressure at the tip of the outer passageway 62 so that as the catheter 60 approaches the ampullae 64, the entire perimeter of the ampullae 64 may be pulled into the outer passageway 62 by the negative pressure suction 65. This pulling of the perimeter of the ampullae 64 may pull the redundant mucosa tout thereby minimizing obscuring wrinkles. A device, for example a catheter, guidewire, papillotome, or contrast injection may then be sent through the inner passageway 63 of the catheter 60, for example, to perform ERCP. Afterwards, the suction 65 may be discontinues to release the ampullae 64 to facilitate removal of the catheter 60. To minimize the risk of undesired engagement of the mucosa, the suction may be inactive during caterer 60 insertion.

Figure 7:
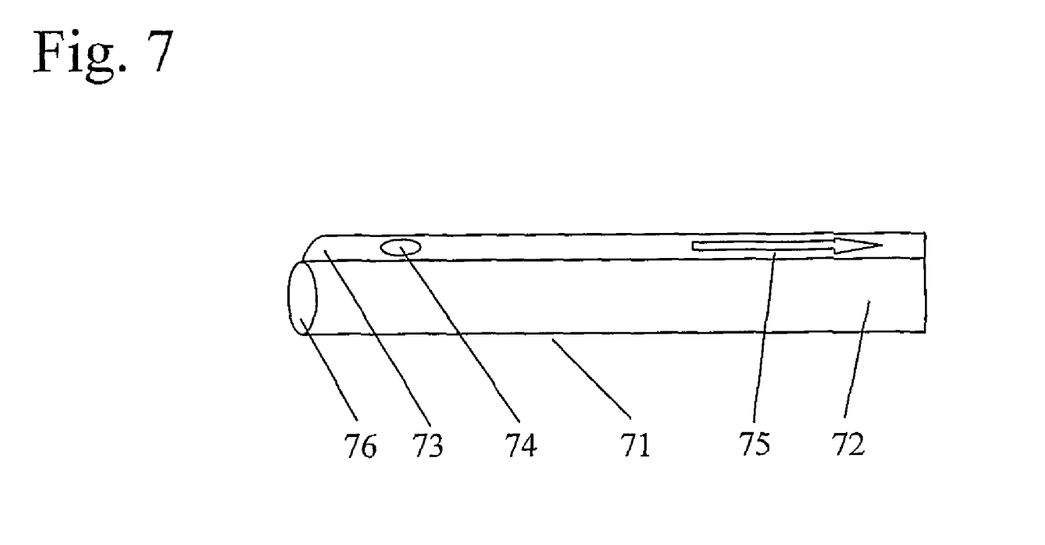
FIG. 7 shows a double-lumen catheter that may be used according to an embodiment of the present invention.

According to another embodiment of the present invention, a double-lumen catheter may be used. An example of such an embodiment is shown in FIG. 7. Here, a double-lumen catheter 71 includes a primary lumen 72 and a secondary lumen 73. Negative pressure suction 75 may be applied to the secondary lumen 73. The secondary lumen may have a single side hole 74 for attaching to the lining inside the orifice at a single point by the force of the suction 75. This single side hole 74 acting as a point of negative pressure. Once the side hole 74 has attached to the lining, the catheter 71 may be pulled back to straighten the redundant mucosa and minimize obstructive wrinkles. A device, for example a catheter, guidewire, papillotome, or contrast injection may then be sent through the primary lumen 72 of the catheter 71 through a front opening 76, for example, to perform ERCP. Afterwards, the suction 75 may be discontinues to release the orifice inner lining to facilitate removal of the catheter 71. To minimize the risk of undesired engagement of the mucosa, the suction may be inactive during caterer 71 insertion.

In embodiments of the present invention that use flaps and/or circumferential anchors, the flat and/or blunt ends of the flaps and/or circumferential anchors may prevent perforation of the mucosa. Additionally, at sufficient tension, for example, when the catheter is removed, the flaps and/or circumferential anchors should be able to buckle over releasing the mucosa. Removal of the catheter should not cause significant trauma to the mucosa.

Figures 8A, 8B, 8C, 8D:
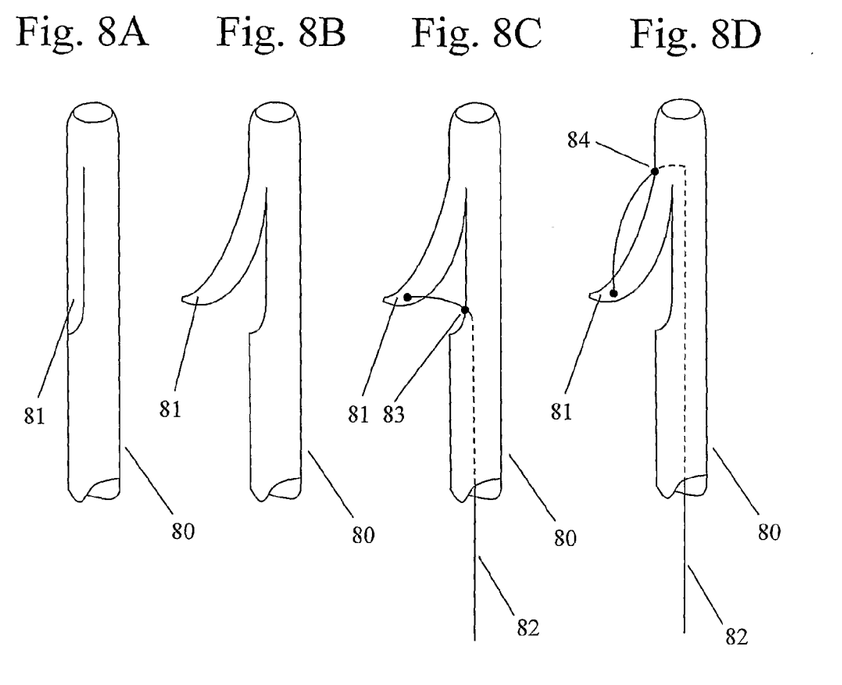
FIGS. 8A-8D show a catheter with a retractable flap according to embodiments of the present invention.

Other embodiments of the present invention may facilitate removal of the catheter by utilizing retractable flaps and/or circumferential anchors. FIGS. 8A-8D show examples of catheters with retractable flaps according to embodiments of the present invention. FIG. 8A shows a catheter 80 with a retractable flap 81 in the retracted position. The flap 81 may be retracted for insertion and/or removal of the catheter. FIG. 8B shows a catheter 80 with a retractable flap 81 in the open position. The flap 81 may be open when engaging the redundant mucosa.

The retractable flap 81 may be biased in either the open position or the closed position. If the flap 81 is biased in the open position, the flap 81 may be pulled closed by a wire 82 that runs the length of the catheter 80 and exits the catheter 80 through a point 83 located behind the flap 81 as shown in FIG. 8C. If the flap 81 is biased in the closed position, the flap 81 may be pulled open by a wire 82 that runs the length of the catheter 80 and exits the catheter 80 through a point 84 above the flap 81 as shown in FIG. 8D. It is to be understood that the catheter 80 may have any number of flap 81 as described above.

Figure 9A:
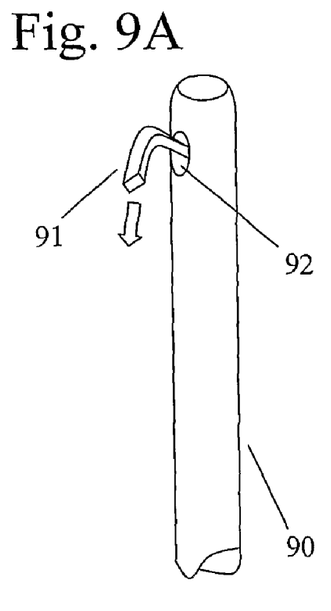
FIGS. 9A and 9B show retractable flaps according to another embodiment of the present invention.
Figure 9B:
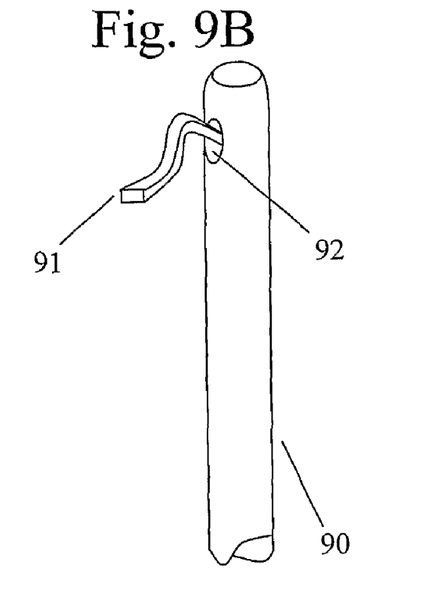

FIGS. 9A and 9B show retractable flaps according to another embodiment of the present invention. The catheter 90 may have a side hole 92. A retractable flap 91 may then be pushed and retracted though the side hole 92 as desired. The retractable flap 91 may be made of a memory-shaped flat wire. FIG. 9A shows such the catheter 90 with a partially extended flap 91 while FIG. 9B shows the catheter 90 with a fully extended flap 91. It is to be understood that the catheter 90 may have any number of flaps 91 as described above.

Embodiments of the present invention may utilize circumferential anchors such as those shown in FIG. 3 that are retractable. Such circumferential anchors may open and close, for example, in an umbrella like fashion.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. A method for inserting a catheter having a primary lumen with a first front opening into a bodily structure, comprising:
   inserting a catheter into the bodily structure;
   activating one or more points of negative pressure on the catheter to engage an inter-mural mucosa of the bodily structure;
   pulling back the catheter thereby pulling the inter-mural mucosa taut and minimizing an obstruction of the first front opening caused by the inter-mural mucosa; and
   inserting a device through the first front opening of the primary lumen of the catheter into the bodily structure.

2. The method of claim 1, wherein the pulling back occurs while the device, comprising a thinner catheter or guidewire, is passed through an internal canal of the bodily structure made taut by the pulling back.

3. A method for inserting a catheter having a primary lumen into a bodily duct structure, comprising:
   inserting a catheter into the bodily duct structure;
   activating one or more points of negative pressure on the catheter to engage an inter-mural mucosa of the bodily duct structure;
   pulling back the catheter thereby pulling the inter-mural mucosa taut; and
   inserting a device through the primary lumen of the catheter into the bodily duct structure.

4. The method of claim 3, wherein the bodily duct structure is a naturally occurring ampullae structure.

5. The method of claim 3, wherein the bodily duct structure is a naturally occurring bile duct structure.

6. The method of claim 3, wherein the bodily duct structure is a naturally occurring pancreatic duct structure.

* * * * *

UNITED STATES PATENT AND TRADEMARK OFFICE
CERTIFICATE OF CORRECTION

| | | |
|---|---|---|
| PATENT NO. | : 8,366,673 B2 | Page 1 of 1 |
| APPLICATION NO. | : 11/883300 | |
| DATED | : February 5, 2013 | |
| INVENTOR(S) | : Reydel | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 877 days.

Signed and Sealed this
Third Day of September, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,366,673 B2  Page 1 of 1
APPLICATION NO. : 11/883300
DATED : February 5, 2013
INVENTOR(S) : Boris Reydel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 967 days.

Signed and Sealed this

First Day of September, 2015

Michelle K. Lee
*Director of the United States Patent and Trademark Office*